United States Patent
Carenzi et al.

[11] Patent Number: 5,080,906
[45] Date of Patent: Jan. 14, 1992

[54] METHOD AND COMPOSITION FOR ORAL ADMINISTRATION OF N-ACETYLCYSTEINE

[75] Inventors: Angelo Carenzi, Busto Arsizio (va); Dario Chiarino; Antonio Longo, both of Monza, all of Italy

[73] Assignee: Zambon Group, S.p.A., Vicenza, Italy

[21] Appl. No.: 558,672

[22] Filed: Jul. 27, 1990

[30] Foreign Application Priority Data

Jul. 27, 1989 [IT] Italy ................ 21339 A/89

[51] Int. Cl.⁵ .................................... A61K 9/48
[52] U.S. Cl. ............................. 424/452; 424/451; 424/465; 424/464; 424/466; 424/479; 424/489; 514/855; 514/885
[58] Field of Search ............... 424/464, 466, 451, 489, 424/479, 452, 465; 514/855, 885

[56] References Cited

U.S. PATENT DOCUMENTS

| 4,081,534 | 3/1978 | Elion et al. | 514/885 |
| 4,867,976 | 9/1989 | Weld et al. | 514/885 |
| 4,877,612 | 10/1989 | Berger et al. | 514/885 |
| 4,894,225 | 1/1990 | Zimmerman | 514/885 |

Primary Examiner—Thurman K. Page
Assistant Examiner—Leon R. Horne
Attorney, Agent, or Firm—Foley & Lardner

[57] ABSTRACT

The blood level of orally administered N-acetylcysteine is substantially increased in a mammal when the N-acetylcysteine is administered in combination with tris(-hydroxymethyl)aminomethane or a pharmaceutically acceptable salt thereof, in a molar ratio of about 1:0.8 to about 1:1.2.

10 Claims, No Drawings

METHOD AND COMPOSITION FOR ORAL ADMINISTRATION OF N-ACETYLCYSTEINE

BACKGROUND OF THE INVENTION

The present invention relates to a method of administration and a pharmaceutical composition containing N-acetylcysteine as the active ingredient which provide increased levels of unmodified drug in the blood following oral administration.

N-acetylcysteine (NAC) also referred to herein as unmodified NAC, (Merck Index Xth Ed., No. 82, Page 13), is used in human therapy for its mucolytic activity. It also possesses several other useful properties including expectorant activity, bronchorrheic and mucoreglatory action, ability to regulate reduced glutathione (GSH) levels, ability to stimulate immune systems debilitated by viral infections, including those debilitated by HIV virus, and its direct or indirect activity as a "free radical scavenger" that may be useful, for example, in the prevention of lung tumors.

Numerous pharmaceutical compositions containing NAC and suitable to a variety of administrative routes have been formulated, including injectable liquids, syrups, tablets, chewable tablets, soluble granulates and effervescent tablets, among others.

For prolonged treatment of several diseases, oral administration is the simplest route of administration and is the one most favored by patients. However, orally administrated NAC is partially degraded or modified in the course of uptake in the intestine and the liver, primarily by deacetylation, reducing its availability in the blood. In a number of therapeutic applications, deacetylated NAC in the bloodstream is less effective or ineffective.

Several salts of NAC, such as those with alkali metals or with basic amino acids, have been described. However, none of these products is able to increase the blood levels of unmodified NAC produced by oral administration.

SUMMARY OF THE INVENTION

It is an object of the invention to provide an orally administrable pharmaceutical form which provides higher levels of unmodified NAC in the blood.

This and other objects of the invention are attained, in a method for treating a mammal, wherein N-acetylcysteine is orally administered to said mammal to achieve a prophylactic or therapeutic result, by providing the improvement comprising orally administering said N-acetylcysteine in combination with tris(hydroxymethyl)aminomethane or a pharmaceutically acceptable salt thereof, in a molar ratio of about 1:0.8 to about 1:1.2, whereby the resultant blood level of unmodified N-acetylcysteine is substantially enhanced.

The invention also provides pharmaceutical compositions suitable for use in the method, including orally administrable formulations containing N-acetylcysteine (NAC) and tris(hydroxymethyl)aminomethane (THAM) as described, together with other desirable, pharmaceutically acceptable components, that lead advantageously upon administration to increased levels of unmodified NAC in the blood.

DETAILED DESCRIPTION

Tris(hydroxymethyl)aminomethane (THAM), (Merck Index Xth Ed., No. 9575, Page 1,395), is a substance with buffering action ("TRIS" buffer), which, due to its safety, is used to increase the aqueous solubility of some acidic drugs, such as aspirin and some prostaglandins. In the case of the THAM salt of the antibiotic Fosfomycin, better bioavailability has also been observed.

As is shown in the examples below, although NAC itself is soluble, its alkaline salts which are very soluble do not provide increased levels of unmodified NAC in the blood. The difficulty in increasing the level of unmodified NAC in the blood does not appear to be insufficient absorption, because high levels of modified NAC in the blood are detected.

Two recent papers [N. Saltzman et al., J. Urol., 136, 846, (1986); J.R. Burns et al., J. Urol., 136, 850, (1986)] report studies of the dissolution of cystein urinary calculi. Both papers describe the use of NAC or THAM solutions or their mixtures. The authors of both papers suggest using the solutions only in irrigating the urinary tract, and the authors of both papers conclude that solutions containing mixtures of NAC and THAM are not more effective than solutions containing NAC or THAM alone.

Surprisingly, we have now found that an orally administrable pharmaceutical composition that contains NAC and THAM in a molar ratio between about NAC:THAM=1:0.8 and 1:1.2, preferably 1:1, together with other additives of common use in the pharmaceutical field, provides higher levels of unmodified NAC in the blood following oral administration.

The indicated molar ratios were determined experimentally to be effective in elevating the blood level of unmodified NAC but should not be construed to exclude slightly higher or lower ratios which may also be effective. However, values far from those enumerated above, such as NAC:THAM=1:0.5 and NAC:THAM=1:2, are not effective.

The unmodified NAC levels obtained by the compositions that are the object of the present invention are significantly higher than those obtained by administering equal amounts of NAC or NAC salts, including the sodium salt, salts with basic amino acids such as lysine and arginine, and the glucosamine salt. The result achieved by the compositions of the invention is particularly surprising in view of the fact that when pharmaceutical compositions containing different molar ratios of NAC and THAM are administered, an increase of the levels of NAC in the blood is not observed. In fact, NAC:THAM molar ratios of 1:0.5, 1:2 and 1:4 are all ineffectual.

Levels of unmodified NAC in the blood of rats and dogs have been determined using a gas chromatography-mass spectrometry system (see Examples 1 and 2).

It is worth noting that after administration of a composition containing NAC and THAM in a molar ratio of 1:1, while a significant increase in the plasma concentration of unmodified NAC is observed, the total amount of NAC absorbed, measured as plasma radioactivity, is not meaningfully different whether NAC is administrated alone or with THAM (see Examples 1 and 2).

This shows that the compositions which are the object of the present invention increase the amount of unmodified NAC in the blood and accordingly increase its effective pharmacological activity without, however, changing its other pharmacokinetic characteristics. In fact, the half-life, and the absorption and elimination constants are substantially the same whether NAC is administered alone or NAC is administered with THAM according to the present invention.

The compositions which are the object of the present invention are prepared using methods well known in the art, by mixing NAC and THAM together with other pharmaceutically acceptable sweeteners, flavorings, excipients and other additives, as may be desired.

THAM and THAM salts suitable for use in the invention are commercially available. Preferred THAM salts are those formed with pharmaceutically acceptable weak acids such as acetate, carbonate, citrate and succinate. The selection of THAM or a salt thereof depends on the pharmaceutical composition to be prepared. For instance, due to the slight hygroscopicity of THAM, for certain solid compositions a less hygroscopic THAM salt might be preferred, according to the usual practice in pharmaceutical technology.

Suitable compositions of the invention include all solid and liquid, orally administrable, pharmaceutical forms, such as tablets, capsules, sugar coated tablets, effervescent tablets, solutions, suspensions, granulates and hydrosoluble granulates, among others.

The compositions that are the objects of the invention will be used in doses suitable to providing effective amounts of NAC, taking into account the higher blood levels of unmodified NAC engendered by the invention. The amount of NAC to be administered to a patient will depend on several parameters, for instance, the kind of disease to be treated. Amounts of from 100 mg to 1.8 g/day will generally be administered for a mucolytic treatment, while amounts of 3-4 g/day or more may be administered for other treatments such as for acute poisoning.

In order to better illustrate the present invention, several examples are presented below. These are meant to be illustrative and should not be construed as limiting the invention.

EXAMPLE 1

Sprague Dawley rats after overnight fast were divided into 7 groups of 33 animals each. These seven groups of animals were treated with different NAC solutions by oral route according to the following scheme:

Group 1-NAC (300 mg/kg) dissolved in water (10 ml/kg)

Group 2-NAC (300 mg/kg) and $NaHCO_3$ (154.6 mg/kg) dissolved in water (10 ml/kg): molar ratio 1:1 (equivalent to 340.4 mg/kg of NAC sodium salt)

Group 3-NAC (300 mg/kg) and THAM (55.6 mg/kg) dissolved in water (10 ml/kg); molar ratio 1:0.25

Group 4-NAC (300 mg/kg) and THAM 111.3 mg/kg) dissolved in water (10 ml/kg); molar ratio 1:0.5

Group 5-NAC (300 mg/kg) and THAM (222.7 mg/kg) dissolved in water (10 ml/kg); molar ratio 1:1

Group 6-NAC (300 mg/kg) and THAM (445.8 mg/kg) dissolved in water (10 ml/kg); molar ratio 1:2

Group 7-NAC (300 mg/kg) and THAM (891.7 mg/kg) dissolved in water (10 ml/kg); molar ratio 1:4

For each group of animals the NAC dose (300 mg/kg) contained $^3$H-NAC in an amount yielding 100 $\mu$Ci/kg. Blood samples were withdrawn just before the treatment and 15, 20, 45, 60, 90, 120, 240, 360, 480 and 1,440 minutes after treatment, via a heparinized syringe. The blood was immediately transferred into plastic tubes containing sodium dithionite (1 mg/5 $\mu$l) and 0.02N sodium EDTA (200 $\mu$l). The plasma was separated by centrifugation at 5,000×g at 4° C. for 20 minutes and the samples thus obtained were stored at −20° C. until the analysis.

Determination of the total unmodified NAC amount

To the plasma samples (0.5 ml) a solution of dithiothreitol (1 mg/kg) in phosphate buffer pH 7.4 (0.1 M) was added. The samples were kept at 37° C. for one hour and then an acetone:formic acid=4:1 (1 ml) mixture was added.

The proteins were separated at 20,000×g for 20 minutes by centrifugation.

To the supernatant 2M HCl (200 $\mu$l) was added and then the NAC was extracted twice with ethyl acetate (6 ml). The organic phases were dried under a stream of nitrogen and, after addition of glutamic acid (10 $\mu$g) as internal stand, the residues were reacted with isopropanol saturated with HCl (200 $\mu$l) at 60° C. for 30 minutes.

At the end of the reaction, excess isopropanol was eliminated and the samples were reacted with 3:1 ethyl acetate:pentafluoropropionic anhydride (200 $\mu$l) at 60° C. for 30 minutes.

After elimination of excess reagent, the residue was dissolved in ethyl acetate (50 $\mu$l) and 1-2 $\mu$l of the solution was injected into the gas chromatography-mass spectrometry system for evaluation of total NAC. Gas chromatographic analysis was carried out on a fused silica capillary column according to the following experimental conditions: column: "linked phase" SE54, l=15 m, internal diameter 0.32 mm; temperature program: 60° C. 50° C./min to 120° C., 25° C./min to 230° C.; injector: on column, carrier gas: He (2 ml/min) elution temperature: 127° C. for internal standard 183° C. for NAC Mass spectrometric analysis was carried out as follows: Instrumentation: Finnigan-MAT 8222, double magnetic and electrostatic sectors, inverse geometry electron impact ionization ionization energy: 70 eV accelerating potential: 3 kV filament current: 3 mA resolution: 1,500 monitored fragment ions: internal standard m/e 230.1 and 248.1 NAC m/e 360.1 and 392.1.

In Table 1 the plasma concentrations of NAC, expressed as $AUC_{0-8h}$, the total NAC detected expressed as g/l, are reported for each group of animals and treatment regimen.

The plasma concentration of NAC is significantly different from that obtained after administration of NAC alone (group 1) only for the group of animals treated with NAC and THAM in the ratio 1:1 (group 5). Animals treated with NAC and THAM in the ratios 1:0.8 and 1:1.2 also show comparable results.

TABLE 1

Plasma concentration of NAC (mg/l) after administration of 300 mg/kg of NAC (containing 100 $\mu$Ci/kg of $^3$H-NAC), alone (group 1) and in combination with $NaHCO_3$ in ratio 1:1 (group 2) or with THAM in ratio 1:0.25 (group 3), 1:0.5 (group 4), 1:1 (group 5), 1:2 (group 6) and 1:4 (group 7).

| | Group 1 NAC | Group 2 NAC-NaHCO$_3$ 1:1 | Group 3 NAC-THAM 1:0.25 | Group 4 NAC-THAM 1:0.5 | Group 5 NAC-THAM 1:1 | Group 6 NAC-THAM 1:2 | Group 7 NAC-THAM 1:4 |
|---|---|---|---|---|---|---|---|
| $AUC_{0-8h}$ | 104.6 ± 3.0 | 105.3 ± 2.8 | 96.9 ± 3.1 | 100.9 ± 3.9 | 135.3 ± 5.7* | 115.9 ± 10.4 | 96.6 ± 1.7 |

TABLE 1-continued

Plasma concentration of NAC (mg/l) after administration of 300 mg/kg of NAC (containing 100 μCi/kg of $^3$H-NAC), alone (group 1) and in combination with NaHCO$_3$ in ratio 1:1 (group 2) or with THAM in ratio 1:0.25 (group 3), 1:0.5 (group 4), 1:1 (group 5), 1:2 (group 6) and 1:4 (group 7).

|  | Group 1 NAC | Group 2 NAC-NaHCO$_3$ 1:1 | Group 3 NAC-THAM 1:0.25 | Group 4 NAC-THAM 1:0.5 | Group 5 NAC-THAM 1:1 | Group 6 NAC-THAM 1:2 | Group 7 NAC-THAM 1:4 |
|---|---|---|---|---|---|---|---|
| (mgh/l) |  |  |  |  |  |  |  |

Notes to table 1:
*p < 0.005 (Student's t)
AUC$_{0-8\,h}$ is Area Under Curve, representing total NAC detected during the 8 hr following administration, expressed as mgh/l.

Determination of total radioactivity

Samples of plasma (50 μl) were added to Lumagel (10 ml), were stirred and were then allowed to stand in the scintillation counter (Beckman LS 8100) at 15° C. for 4 hours. Radioactivity was measured after the stabilization time.

The total radioactivity in plasma after administration of 300 mg/kg of NAC (containing 100 μCi/kg of $^3$H-NAC) (group 1) and after administration of the same amount of NAC with THAM in the ratio 1:1 (group 5) are reported in Table 2.

TABLE 2

Plasma concentration (mg/l) of total radioactivity after administration of 300 mg/kg of NAC (containing 100 μCi/kg of $^3$H-NAC) (group 1) and after administration of the same amount of NAC with THAM in the ratio 1:1 (group 5).

|  | Group 1 NAC | Group 5 NAC-THAM 1:1 |
|---|---|---|
| AUC$_{0-24\,h}$ mgh/l | 4048.3 ± 105.9 | 4243.1 ± 59.3 |

From the data reported in Table 2 it is evident that the total radioactivity present in the plasma of the animals of group 1 and of group 5 is not meaningfully different, i.e., absorbed NAC is substantially the same when NAC is administered alone (group 1) or in combination with THAM in the ratio 1:1 (group 5). AUC$_{0-24h}$ is the cumulative total of NAC detected over the time period from 0 to 24 hrs. after administration, expressed as mgh/l.

EXAMPLE 2

Male Beagle dogs were fasted overnight and were divided into 4 groups of 4 animals each. The four groups were treated orally with different NAC solutions according to the following scheme:

Group 1-NAC (50 mg/kg) dissolved in water (1 ml/kg)

Group 2-NAC (50 mg/kg) and THAM (37.11 mg/kg) (molar ratio NAC:THAM=1:1) dissolved in water (1 ml/kg)

Group 3-NAC lysinate (94.79 mg/kg, corresponding to 50 ml/kg of NAC) dissolved in water (1 ml/kg)

Group 4-NAC glucosamine salt (10,489 mg/kg, corresponding to 50 mg/kg of NAC) dissolved in water (1 ml/kg).

For each group of animals the dose of NAC (50 ml/kg) contained an amount of $^{14}$C-NAC equal to 20 μCi/kg.

Blood samples were withdrawn by a heparinized syringe just before the treatment and 10, 20, 30, 45, 60, 120, 240, 360, 480 and 1,440 minutes after treatment.

The blood samples were treated and stored according to the same procedure described in Example 1.

The determination of unmodified NAC in the plasma and of total radioactivity in the plasma were carried out according to the procedures described in Example 1.

The results are reported in Tables 3 and 4.

TABLE 3

Plasma concentration of NAC (mg/l) after administration of 50 mg/kg of NAC (containing 20 μCi/kg of $^{14}$C-NAC), alone (group 1), in combination with THAM in ratio 1:1 (group 2), NAC-lysinate (group 3) and NAC-glucosamine salt (group 4). AUC$_{0-\infty}$ is the cumulative total NAC detected over the entire time course, expressed as mgh/l.

|  | Group 1 NAC | Group 2 NAC-THAM 1:1 | Group 3 NAC-lysinate 1:1 | Group 4 NAC-glucosamine 1:1 |
|---|---|---|---|---|
| AUC$_{0-\infty}$ (mgh/l) | 57.53 ± 7.29 | 90.6 ± 10.81* | 73.37 ± 10.33 | 55.48 ± 6.21 |

Notes to Table 3:
*p < 0.02 (Student's t)

TABLE 4

Plasma concentration (mg/l) of total radioactivity after oral administration in the dog of 50 mg/kg of NAC (containing 20 μCi/kg of $^{14}$C-NAC) (group 1) and after administration of the same amount of NAC with THAM in the ratio 1:1 (group 2), NAC-lysinate (group 3) and NAC-glucosamine (group 4). AUC$_{0-24\,h}$ is the cumulative total NAC detected during the 24 hr. following administration, expressed as mgh/l.

|  | Group 1 NAC | Group 2 NAC-THAM 1:1 | Group 3 NAC-lysinate 1:1 | Group 4 NAC-glucosamine 1:1 |
|---|---|---|---|---|
| AUC$_{0-24\,h}$ | 1864.13 ± 856.57 | 1170.63 ± 189.84 | 1247.23 ± 185.18 | 1394.59 ± 106.11 |

TABLE 4-continued

Plasma concentration (mg/l) of total radioactivity after oral administration in the dog of 50 mg/kg of NAC (containing 20 μCi/kg of $^{14}$C-NAC) (group 1) and after administration of the same amount of NAC with THAM in the ratio 1:1 (group 2), NAC-lysinate (group 3) and NAC-glucosamine (group 4). $AUC_{0-24\,h}$ is the cumulative total NAC detected during the 24 hr. following administration, expressed as mgh/l.

| | Group 1 NAC | Group 2 NAC-THAM 1:1 | Group 3 NAC-lysinate 1:1 | Group 4 NAC-glucosamine 1:1 |
|---|---|---|---|---|
| (mghl$^{-1}$) | | | | |

From the data reported in Table 3 it is evident that the administration of NAC and THAM together in the ratio 1:1 can increase the amount of unmodified NAC in the plasma with respect to NAC administered alone, whereas NAC lysine or glucosamine salts do not provide plasma levels meaningfully different from those of NAC itself.

The data in Table 4 show that the total amount of absorbed NAC is not different if NAC is administered as such or together with an equimolecular amount of THAM, or as the lysine or glucosamine salt.

EXAMPLE 3

The following compositions for oral administration were prepared:

Solution

Each small bottle contains:
NAC 200 mg
THAM 148 mg
EDTA 2 mg
Sorbitol 3 g
Purified water q.s. to 10 ml The ingredients were dissolved in purified water and then the solution was distributed into small glass bottles and suitably sealed.

Granulate

Each bag contains:
NAC 200 mg
THAM 119 mg
Gum arabic 100 mg
Dextrose 300 mg
Fruit flavor 50 mg
Saccharin 5 mg
Saccharose 2,226 mg NAC and THAM were first granulated separately in mixtures with gum arabic and dextrose. The granulates were dried and then mixed together with saccharin, saccharose and flavour and then distributed into the bags.

Solution

Each bag contains:
NAC 100 mg
THAM 74 mg
EDTA 3 mg
Citrus fruit flavor 50 mg
Saccharose 3 g
Purified water q.s. to 10 ml The ingredients were dissolved in purified water and then the solution was distributed into bags.

Granulate

Each small bottle contains:
NAC 3.0 g
THAM 1.780 g
Methyl p-hydroxybenzoate 0.150 g
Propyl p-hydroxybenzoate 0.035 g
Colouring agent 0.007 g
Orange flavor 2.000 g
Sorbitol 63.028 g THAM was blended with the preservatives, the colouring agent and sorbitol. The blend was then mixed with water, granulated and dried. NAC and flavor were added and the granulate was distributed into amber coloured small glass bottles.

Chewable tablets

Each tablet contains:
NAC 600 mg
THAM 534 mg
Gum arabic 200 mg
Dextrose 600 mg
Citrus fruit flavour 100 mg
Saccharin 15 mg
Mannitol 251 mg NAC and THAM were granulated separately with an aqueous solution of gum arabic and dextrose. The granulate was dried, mixed with flavour, saccharin and mannitol and pressed into tablets. A similar composition was prepared by replacing THAM with THAM carbonate (807 mg, corresponding to 534 mg of THAM).

From the foregoing description, one of ordinary skill in the art can easily ascertain the essential characteristics of this invention and, without departing from the spirit and scope thereof, can make various changes and modifications of the invention to adapt it to various usages and conditions.

What is claimed is:

1. In a method for treating a mammal, wherein N-acetylcysteine is orally administered to said mammal to achieve a prophylactic or therapeutic result,
    the improvement comprising orally administering said N-acetylcysteine in combination with tris(hydroxymethyl)aminomethane or a pharmaceutically acceptable salt thereof, in a molar ratio of about 1:0.8 to about 1:1.2, whereby the resultant blood level of unmodified N-acetylcysteine is substantially enhanced.

2. The method of claim 1, wherein the molar ratio of N-acetylcysteine to tris(hydroxymethyl)aminomethane is about 1:1.

3. The method of claim 1, wherein said resultant enhanced blood level is at least about 20% higher in the first 8 hours after said oral administration than for administration of N-acetylcysteine alone.

4. The method of claim 3, wherein said resultant enhanced blood level is at least about 35% higher in the first 8 hours after said oral administration than for administration of N-acetylcysteine alone.

5. The method of claim 3, wherein said resultant enhanced blood level is at least about 50% higher in the first 8 hours after said oral administration than for administration of N-acetylcysteine alone.

6. The method of claim 1, wherein said resultant enhanced blood level is at least about 20% higher in the first 8 hours after said oral administration than for administration of a basic amino acid salt or a glucosamine salt of N-acetylcysteine.

7. The method of claim 1, wherein said oral administration is in the form of a tablet or capsule or an aqueous solution or suspension.

8. A pharmaceutical composition, comprising in admixture N-acetylcysteine and tris(hydroxymethyl)aminomethane or a pharmaceutically acceptable salt thereof, in a molar ratio of about 1:0.8 to about 1:1.2, and at least one pharmaceutically acceptable sweetener, flavoring ingredient or excipient for oral administration.

9. The composition of claim 8, wherein said molar ratio is about 1:1.

10. The composition of claim 8, which is in the form of a tablet, capsule, effervescent tablet, granulate or hydrosoluble granulate or an aqueous solution or suspension.

* * * * *